| (12) | United States Patent | (10) Patent No.: | US 8,431,093 B2 |
|---|---|---|---|
| | Rosselle | (45) Date of Patent: | Apr. 30, 2013 |

(54) DEVICE FOR CENTERING A MICROTITER PLATE

(75) Inventor: Pascal Rosselle, Morlaas (FR)

(73) Assignee: Gilson SAS, Villiers le Bel (FR)

( * ) Notice: Subject to any disclaimer, the term of this patent is extended or adjusted under 35 U.S.C. 154(b) by 631 days.

(21) Appl. No.: 12/632,440

(22) Filed: Dec. 7, 2009

(65) Prior Publication Data

US 2010/0143200 A1 Jun. 10, 2010

(30) Foreign Application Priority Data

Dec. 10, 2008 (FR) .................................. 08 58440

(51) Int. Cl.
*B01L 9/00* (2006.01)
*B23Q 3/00* (2006.01)

(52) U.S. Cl.
USPC ................. 422/566; 422/500; 248/346.03

(58) Field of Classification Search ................. 422/404, 422/560, 561, 566, 500; 356/399–401; 248/346.03
See application file for complete search history.

(56) References Cited

U.S. PATENT DOCUMENTS

| 4,701,754 A | * | 10/1987 | Provonchee | ............ | 340/815.45 |
| 5,294,795 A | * | 3/1994 | Lehtinen et al. | ............ | 250/328 |
| 6,474,181 B2 | | 11/2002 | Gilson et al. | | |
| 7,222,431 B1 | | 5/2007 | Norton et al. | | |
| 2003/0017083 A1 | | 1/2003 | Pobering et al. | | |

FOREIGN PATENT DOCUMENTS

| EP | 1 111 391-0 | 6/2001 |
| WO | WO-01/96880-0 | 12/2001 |

OTHER PUBLICATIONS

EP Communication issued in European Patent Application No. 09796796.2 and dated Jul. 22, 2011.
International Preliminary Report on Patentability issued in PCT/IB2009/007653 and mailed Jun. 23, 2011.
International Search Report and Written Opinion issued in PCT/IB2009/007653 and mailed Mar. 31, 2010.
International Preliminary Report on Patentability issued in PCT/IB2009/007653 and mailed on Mar. 31, 2010.
Preliminary Search Report for French Patent Application No. 0858440 dated Jul. 30, 2009.
Communication from the European Patent Office on EP Application 09796796.2, mailed May 2, 2012.

* cited by examiner

*Primary Examiner* — In Suk Bullock
*Assistant Examiner* — Paul Hyun
(74) *Attorney, Agent, or Firm* — Foley & Lardner LLP (57) ABSTRACT

A pipetting aid device includes a support comprising a face, a plurality of light elements mounted in the support forming a two-dimensional array in the plane of the face, and first and second centering structures. The first and second centering structures are mounted to extend from the face of the support. The first centering structure includes a first and second pair of stop walls, wherein a pair of stop walls forms a corner. The second centering structure includes a third and fourth pair of stop walls. The first and third pairs of stop walls form corners of a first positioning zone of a first type of plate. The second and fourth pairs of stop walls form corners of a second positioning zone of a second type of plate. The first centering structure and the second centering structure are positioned outside both the first positioning zone and the second positioning zone.

20 Claims, 6 Drawing Sheets

DEVICE FOR CENTERING A MICROTITER PLATE

CROSS-REFERENCE TO RELATED APPLICATIONS

This application claims priority under the Paris Convention to French Application No. 0858440, filed Dec. 10, 2008, the disclosure of which is incorporated by reference herein in its entirety.

FIELD

The present application relates to the field of pipetting aid devices of the type comprising a microtiter plate support or a test tube support plate fitted with an array of light elements that can be switched on and off as a liquid is dispensed or drawn off from the wells or test tubes in the plate.

BACKGROUND

Pipetting aid devices comprising a microtiter plate support or a test tube support plate are known that comprise an array of light elements such as light emitting diodes, and means for controlling these light elements, for example, formed from control keys and/or buttons. These devices are usually designed to hold microtiter plates with standard dimensions comprising an array of wells, the number of which is generally a multiple of 6 wells per row and 4 wells per column. Thus, in example embodiments, plates with 24×16 (384) wells and plates with 12×8 (96) wells are used.

The layout of wells on typically used microtiter plates varies as a function of the number of wells in these plates. The array of wells relative to the edges of the plate is offset from one plate to another, depending on the number of wells in each plate. The diameter of the well section can also vary from one type of plate to another. Thus, plates comprising a relatively small number of wells can contain wells with a larger cross-section than wells in plates comprising a larger number of wells.

To operate satisfactorily, a pipetting aid device of the type described has a light element or an arrangement of light elements facing each well in the microtiter plate that it supports. Consequently, microtiter plates are associated with assembly adaptors if they have to be installed on known pipetting aid devices. More precisely, each type of microtiter plate is characterized by the arrangement of wells in the plate, and is commonly used with an adaptor comprising:

a lower face provided with means designed to cooperate with centering means supported on pipetting aid device supports;

an upper face comprising plate centering means, arranged to enable an alignment of wells in plates of the type associated with this adaptor, with at least some of the light elements of pipetting aid devices; and a array of orifices that connect the lower face to the upper face of the adaptor and that are intended to allow light emitted by light elements of the pipetting aid devices to reach the wells of the microtiter plates.

However, the change of the adaptor that must accompany each change in the type of microtiter plate is tedious for the user. Furthermore, a set of adaptors associated with each plate in a given set of microtiter plates is required which introduces a major extra cost and is not very practical.

SUMMARY

In an example embodiment, a pipetting aid device is provided. The device includes, but is not limited to, a support comprising a first face, a plurality of light elements mounted in the support to form a two-dimensional array in the plane of the first face, a first centering structure, and a second centering structure. The first centering structure is mounted to extend from the first face of the support and includes at least a first pair and a second pair of stop walls, wherein a pair of stop walls forms a corner. The second centering structure is mounted to extend from the first face of the support and includes at least a third pair and a fourth pair of stop walls. The first pair of stop walls and the third pair of stop walls form corners of a first positioning zone of a first type of plate. The second pair of stop walls and the fourth pair of stop walls form corners of a second positioning zone of a second type of plate. The first centering structure and the second centering structure are positioned outside both the first positioning zone and the second positioning zone.

Other principal features and advantages of the invention will become apparent to those skilled in the art upon review of the following drawings, the detailed description, and the appended claims.

BRIEF DESCRIPTION OF THE DRAWINGS

Example embodiments of the invention will hereafter be described with reference to the accompanying drawings, wherein like numerals denote like elements.

DETAILED DESCRIPTION

Figure 1:
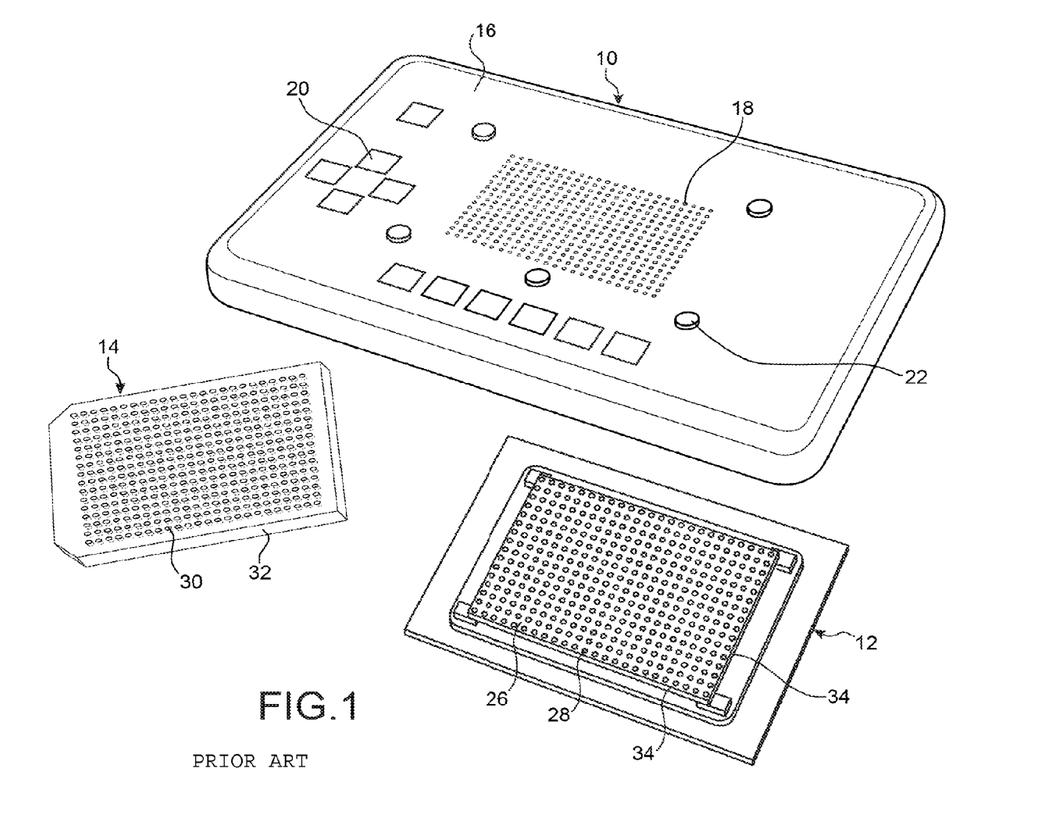
FIG. 1 depicts a diagrammatic perspective view of a known kit comprising a pipetting aid device, an adaptor, and a microtiter plate.

With reference to FIG. 1, a kit that comprises a pipetting aid device 10, an adaptor 12, and a microtiter plate 14 designed to facilitate manual pipetting operations is shown in accordance with an example embodiment. The pipetting aid device 10 comprises a support 16 comprising an array of light elements 18, means for controlling the light elements 18 including control keys 20 and adaptor centering pins 22. In the illustrated example, there are 384 light elements 18 distributed in a two-dimensional (2D) array of 24 columns and 16 rows.

The adaptor 12 comprises a lower face that has a periphery provided with assembly orifices (not shown) designed to cooperate with pins 22 of the device 10, and an upper face 26 designed to hold the microtiter plate 14. The adaptor 12 also comprises an array of orifices 28 that connect its lower face 24 to its upper face 26 and which, for example, include 384 orifices arranged in a manner similar to the arrangement of the light elements 18 of device 10.

The microtiter plate 14 comprises an array of wells 30 configured to hold a liquid during pipetting operations, and a flanged edge 32 with standard dimensions configured to enable centering of the plate 14 on the adaptor 12. For example, there may be 384 wells 30 arranged in a manner similar to the arrangement of the light elements 18 of the device 10.

The edges 34 of the upper face 26 of the adaptor 12 are arranged in a manner which enables positioning of the wells 30 of the plate 14 facing the light elements 18 of the device 10. Thus, when the plate 14 is fitted on the adaptor 12 and the adaptor is positioned on the pipetting aid device 10, each well 30 in the plate may be illuminated by a light element 18 of the device 10. During pipetting operations, the operator can thus successively switch the light elements 18 on and off so as to illuminate the well 30 on which the operator is taking action at any time.

Figure 2:
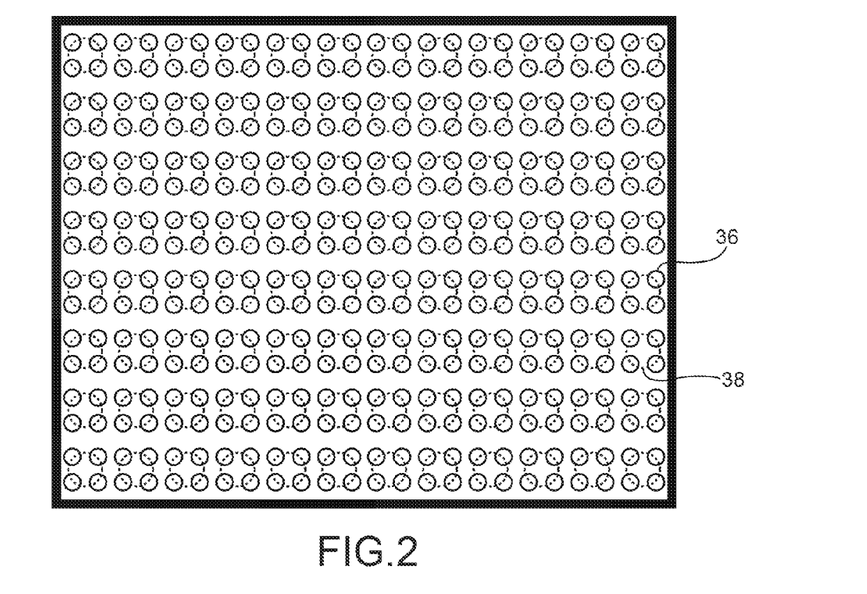
FIG. 2 depicts a diagrammatic top view of a microtiter plate illustrating an offset array of orifices of first and second microtiter plates of different types.

The device 10 may be used as a microtiter plate support comprising a smaller number of wells 30. However, the difference in the number of wells 30 between two microtiter plates is usually accompanied by an offset of the array of wells of these plates relative to the edges of the plates, as shown with reference to FIG. 2. In FIG. 2, the small circles 36 represent the location of the 384 wells in the plate 14, while the large circles 38 represent the location of the wells in the second plate that comprises 96 wells.

As shown in FIG. 2, the wells 38 in the second plate are positioned on the centers of the squares each of which is formed by four wells 36 of the first plate. In other words, the array of wells 38 in the second plate is offset from the array of wells 36 in the first plate relative to the edges of the second plate by a distance equal to half the interval separating two wells 36 of the first plate along each of the two directions of the array. Therefore, a second adaptor arranged to enable an equivalent offset of the second plate relative to the position occupied by the first plate is necessary when the second plate is fitted on the first adaptor 14, so that the wells 38 in the second plate can be correctly positioned relative to the light elements 18 of the pipetting aid device 10.

Figure 3:
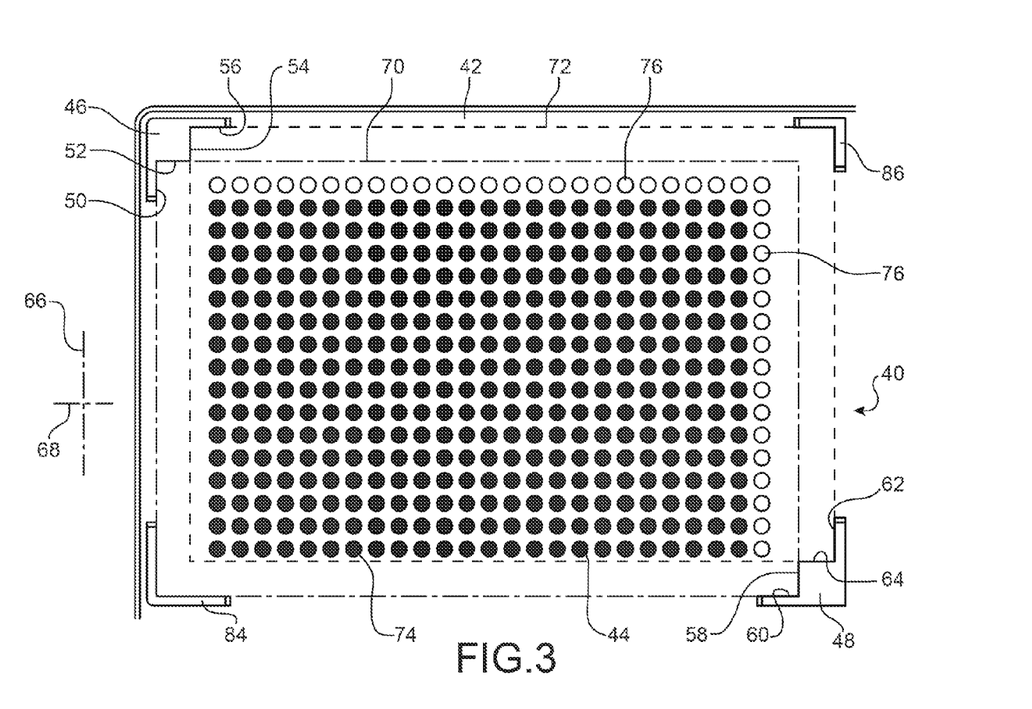
FIG. 3 shows a diagrammatic top view of a pipetting aid device illustrating cooperation with the first microtiter plate in FIG. 2 in accordance with a first example embodiment.

FIG. 3 diagrammatically shows a pipetting aid device 40 comprising a support 42 which includes an array of light elements 44 and module centering means. In an example embodiment, the array of light elements 44 may be formed of light emitting diodes, and a module may include a microtiter plate, a test tube support plate, etc. The support 42, the array of light elements 44, and the module centering means form an assembly. The device 40 also comprises means for controlling the array of light elements 44. These means are not visible in FIG. 3, and may include for example an input interface, a communication interface, a computer-readable medium, a processor, and a control application.

The input interface provides an interface for receiving information from the operator for entry into pipetting aid device 40 as known to those skilled in the art. The input interface may use various input technologies including, but not limited to, a keyboard, a pen and touch screen, a mouse, a track ball, a touch screen, a keypad, one or more buttons, etc. to allow the operator to enter information into pipetting aid device 40 or to make selections presented in a user interface displayed on a display. The input interface may provide both an input and an output interface. For example, a touch screen both allows operator input and presents output to the operator. Pipetting aid device 40 may have one or more input interfaces that use the same or a different input interface technology.

The computer-readable medium is an electronic holding place or storage for information so that the information can be accessed by the processor as known to those skilled in the art. The computer-readable medium can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Pipetting aid device 40 may have one or more computer-readable media that use the same or a different memory media technology. Pipetting aid device 40 also may have one or more drives that support the loading of a memory media such as a CD or DVD.

The communication interface provides an interface for receiving and transmitting data between devices using various protocols, transmission technologies, and media as known to those skilled in the art. The communication interface may support communication using various transmission media that may be wired or wireless. Pipetting aid device 40 may have one or more communication interfaces that use the same or a different communication interface technology. Data may be transferred between pipetting aid device 40 and other devices using the communication interface thereby providing connectivity to other systems. For example, the communication interface may communicate with filling sensors onboard the pipettes to enable automatic monitoring of pipetting operations.

The processor executes instructions as known to those skilled in the art. The instructions may be carried out by a special purpose computer, logic circuits, or hardware circuits. Thus, the processor may be implemented in hardware, firmware, software, or any combination of these methods. The term "execution" is the process of running an application or the carrying out of the operation called for by an instruction. The instructions may be written using one or more programming language, scripting language, assembly language, etc. The processor executes an instruction, meaning that it performs the operations called for by that instruction. The processor operably couples with the input interface, with the computer-readable medium, and with the communication interface to receive, to send, and to process information. The processor may retrieve a set of instructions from a permanent memory device and copy the instructions in an executable form to a temporary memory device that is generally some form of RAM. Pipetting aid device 40 may include a plurality of processors that use the same or a different processing technology.

The control application performs operations associated with control of the array of light elements 44. The control application may receive input through the input interface so that a user can inform pipetting aid device 40 about the type of microtiter plate or test tube support plate so that the control application can adapt the operating mode of the array of light elements 44 accordingly. As a variant, the control application may be associated with module presence sensors arranged on different module reception zones or more generally associated with any type of module identification means to automatically adapt the behavior of the light elements 44 as a function of the type of module used. The control application may be written using one or more programming languages, assembly languages, scripting languages, etc.

The module centering means comprise two centering structures 46 and 48 mounted on the support 42, for example, by welding or screwing. As used herein, the term "mount" includes join, unite, connect, associate, insert, hang, hold, affix, attach, fasten, bind, paste, secure, bolt, screw, rivet, solder, weld, press against, formed with, glue, and other like terms. Centering structures 46, 48 may be removably mounted to the support 42, or the support may comprise recesses into which the centering structures 46, 48 may be retracted by any appropriate type of means. The removable attachment mode may be provided by any appropriate means such as an elastic clip fit. Retracting the centering structures 46, 48 reduces the size of the device to facilitate transport and storage of pipetting aid device 40.

Each of the centering structures 46 and 48 has four stop walls 50 to 64 that extend perpendicular to the plane of the support 42 and that are configured to cooperate with the rectangular edges of a microtiter plate or a test tube support plate during positioning of such a plate on the support 42 so that the plate can be centered. The stop walls 50 to 64 of the centering structures 46 and 48 form a stepped surface on each of the centering structures 46, 48.

Two stop walls 50 and 54 of the first centering structure 46, and two stop walls 58 and 62 of the second centering structure 48, extend along a first direction 66 of the two directions of the 2D array of light elements 44, while two other stop walls 52 and 56 of the first centering structure 46, and two other stop walls 60 and 64 of the second centering structure 48, extend along a second direction 68 of the two directions of the 2D array of light elements 44.

The corner surfaces formed firstly by the walls 50 and 52 of the first centering structure 46, and secondly by the walls 58 and 60 of the second centering structure 48, each form a means for centering a microtiter plate of a first type comprising 384 wells, in a position in which such a plate covers a first rectangular zone 70 of the support 42. These centering means are arranged at the ends of one of the diagonals of this zone 70, outside said zone 70. The stop walls 50, 52, 58 and 60 thus form a first group of centering means that are designed for centering the microtiter plates of the first type.

In a similar manner, each of the corner surfaces formed firstly by the walls 54 and 56 of the first centering structure 46, and secondly by the walls 62 and 64 of the second centering structure 48, each form a means for centering a microtiter plate of a second type comprising 96 wells in a position in which such a plate covers a second rectangular zone 72 of the support 42, and these centering means are arranged at the ends of one of the diagonals of this zone 72, outside said zone 72. The stop walls 54, 56, 62 and 64 thus form a second group of centering means that will be used for centering plates of the second type. First rectangular zone 70 and second rectangular zone 72 correspond to module reception zones for the microtiter plates of the first and second type.

In the example embodiment of FIG. 3, the separation of stop wall 54 from stop wall 50 and the separation of stop wall 62 from stop wall 58 along second direction 68 orthogonal to stop walls 54, 50, 62, and 58 is approximately equal to 1.5 times the interval separating two consecutive light elements 44 of the device 40 along the second direction 68. Similarly, the separation of the stop wall 56 from stop wall 52 and the separation of stop wall 64 from the stop wall 60 along the first direction 66 orthogonal to stop walls 56, 52, 64, and 60 is approximately equal to 1.5 times the interval separating two consecutive light elements 44 of the device 40 along the first direction 66. The stop walls of centering structures 46, 48, respectively, make it possible to make wells of the two types of plates coincide with the light elements 44 of the device 40, while allowing a large width of stop walls 52 and 64 and of stop walls 54 and 58. In an example embodiment, the width of these stop walls is limited by the value of the above-mentioned separations between the walls so that these walls do not extend over the module reception zones 70 and 72. The large width of the above-mentioned walls allows these walls to efficiently hold the modules in their centering position on the support 42.

FIG. 3 shows solid disks 74 symbolizing those light elements 44 which are aligned with the 384 wells in the first type of plate when such a plate is installed on the support 42 and is centered on zone 70 of support 42 by stop walls 50, 52, 58 and 60 forming the first group of centering means. The array of light elements 44 comprises an additional row and column 76 of light elements symbolized by empty circles that are not used with the first type of plate, but that are used with the second type of plate.

Figure 4:
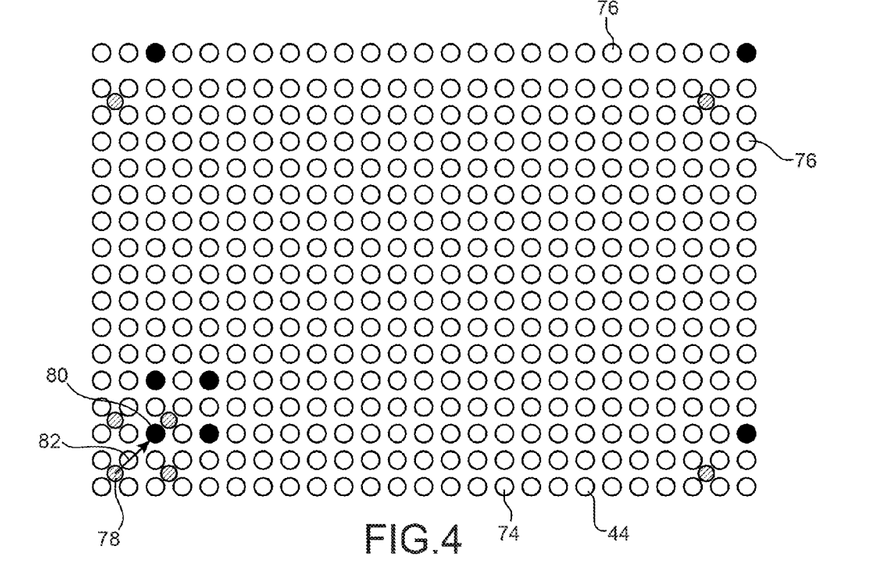
FIG. 4 illustrates a position of the second microtiter plate in FIG. 2 on the pipetting aid device shown in FIG. 3 in accordance with the first example embodiment.

FIG. 4 shows the position of a second type of a plate relative to the light elements 44 of the device 40. In FIG. 4, the locations of some of the 96 wells of a plate of the second type are shown by cross-hatched disks 78, if such a plate is positioned on the first zone 70 of the support 42 and is centered by the stop walls 50, 52, 58 and 60. The solid disks 80 in FIG. 4 symbolize the locations of the wells of the plate of the second type when this type of plate is placed on the second zone 72 of the support and is centered by the stop walls 54, 56, 62 and 64. Thus, positioning of the second type of plate on the second zone 72 of the support positions the wells above the array of light elements 44.

The arrow 82 indicates the offset between the two zones 70 and 72 of the support 42, the amplitude of which is equal to 1.5 times the interval separating two adjacent light elements 44 along each of the directions of the array of light elements 44 so as to align the wells of the plate with the light elements 44. An offset of 0.5 times the interval separating two adjacent light elements 44 also allows alignment of the wells in the second type of plate with the light elements 44. However, a larger amplitude offset may increase the extent of stop walls 52 and 64 and stop walls 54 and 58, and thus enables these walls to provide good support to the microtiter plate installed on the device 40, including in the case in which the edges of the plate have rounded corners, insofar as the radius of curvature of these corners is approximately equal to half the interval separating two adjacent light elements 44. However, a larger amplitude offset results in the addition of a column and a row of light elements 76 to allow the array of light elements 44 to cover all wells in the second type of plate.

Figure 5:
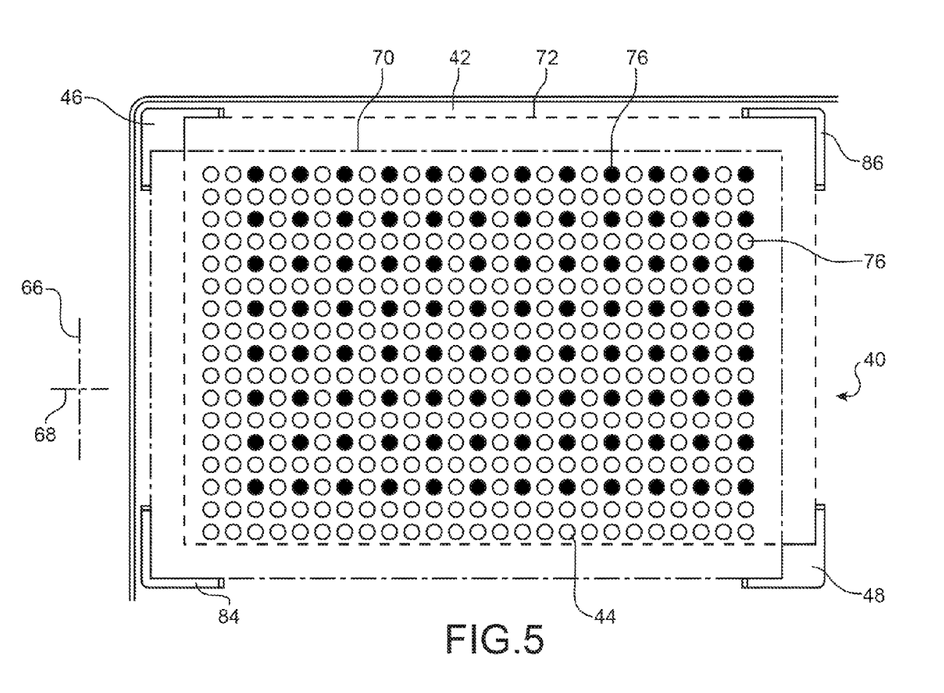
FIG. 5 shows a diagrammatic top view of the pipetting aid device of FIG. 3 illustrating cooperation with the second microtiter plate in FIG. 2 in accordance with a first example embodiment.

FIG. 5 shows the positions of the 96 wells of the second type of plate relative to the array of light elements 44. The device 40 also optionally comprises second centering structures 84 and 86 each arranged in a corner of the first zone 70 and in a corner of the second zone 72, respectively and distinct from the corners at which the centering structures 46 and 48 are arranged. Centering structures 46 and 48 are diagonally arranged with respect to each other and second centering structures 84 and 86 are diagonally arranged with respect to each other.

Second centering structures 84 and 86 may also be adapted for centering a third type of microtiter plate comprising 24 wells for which the positions of the wells are offset by 1.5 times the interval separating two adjacent light elements 44, according to the directions 66, 68 of the array of light elements 44 relative to the positions of the wells in the first type of plate. This offset is the same as the offset provided between the first zone 70 and the second zone 72 of the support 42.

Figure 6:
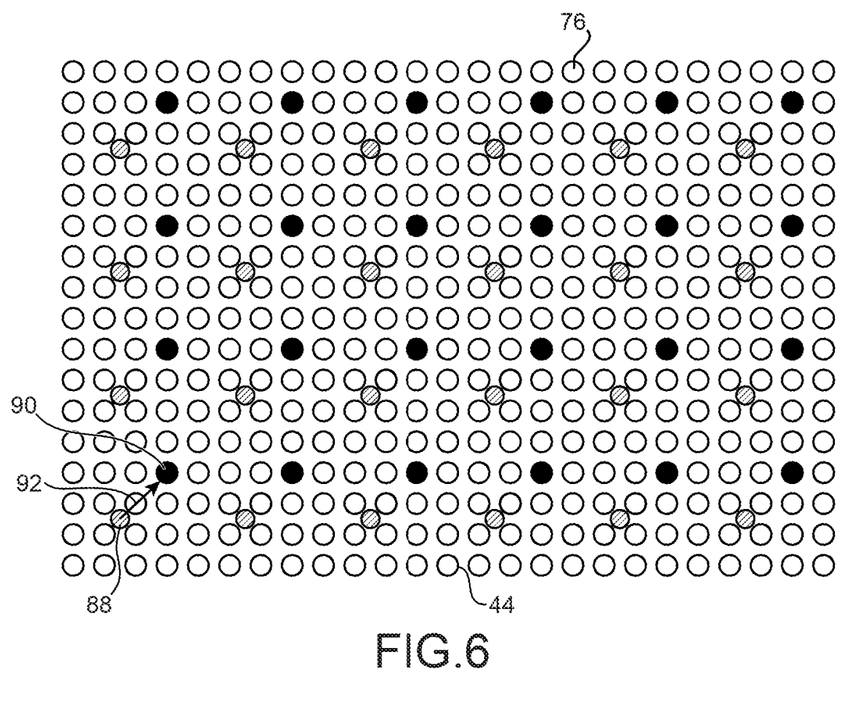
FIG. 6 illustrates a position of a third microtiter plate on the pipetting aid device shown in FIG. 3 in accordance with the first example embodiment.
Figure 7:
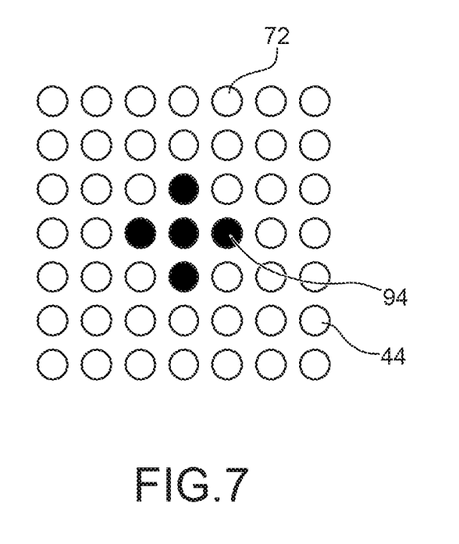
FIG. 7 illustrates an operating mode of the pipetting aid device of FIG. 3 for use with a fourth microtiter plate on the pipetting aid device shown in FIG. 3 in accordance with the first example embodiment.

FIG. 6 shows the position of the third type of microtiter plate relative to the array of light elements 44 in the device 40 where the positions of the wells in the third type of microtiter plate are indicated by cross-hatched disks 88 when the third type of microtiter plate is in the position defined by the first group of centering means, and by solid disks 90 when the plate is centered by the second group of centering means, respectively. Thus, either group of centering means may be used to position the third type of microtiter plate relative to the array of light elements 44 in the device 40. The arrow 92 indicates how the offset between the two zones 70 and 72 of the support 42 makes it possible to arrange wells in the third type of plate so that they coincide with some of the light elements 44. An additional row and column 76 of light elements is not needed in the case in which a plate of this third type is used. When using a plate for which the wells have a sufficiently large cross section to cover several light elements 44, it is possible to illuminate each well in the plate by several light elements 94 as shown in FIG. 7.

Figure 8:
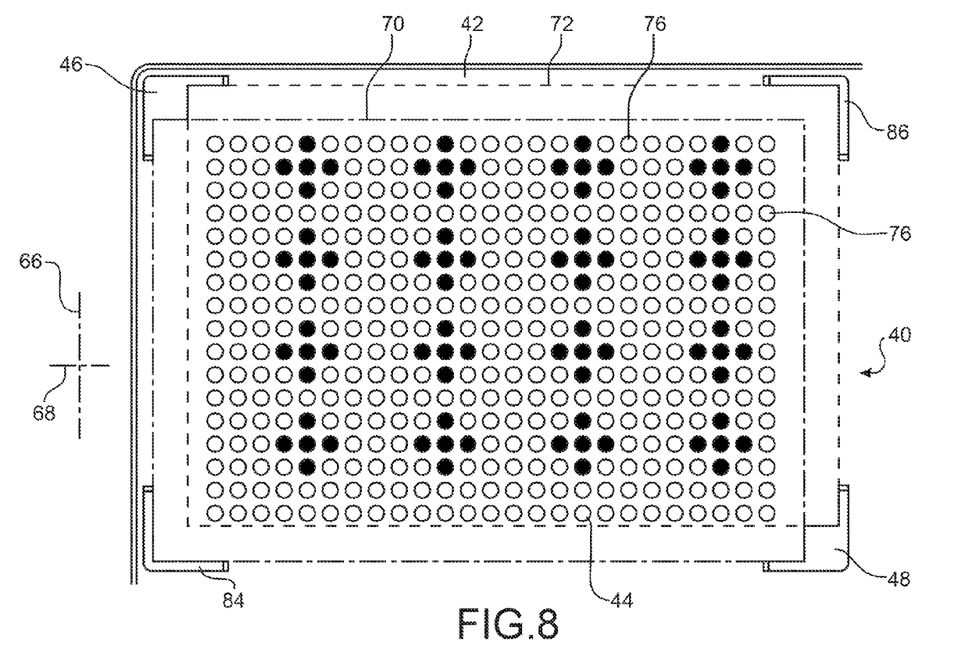
FIG. 8 shows a diagrammatic top view of the pipetting aid device of FIG. 3 illustrating cooperation with the fourth microtiter plate in accordance with a first example embodiment.

As an example, FIG. 8 shows the way in which the 16 wells of a fourth type of plate may be illuminated by groups of light elements 94 indicated by solid disks when such a plate is located on the second zone 72 of the support 42. In this example, each group of light elements 94 comprises a central light element, for which the light emission axis coincides with the axis of the corresponding well of the plate. However, different configurations are also possible. For example, each group of light elements 94 does not necessarily include a central light element located on the center line of the corresponding well on the plate, but rather a layout of light elements distributed around this axis.

The spacing between the wells in the plates may not be the same along both directions of the array of light elements 44, as shown in FIG. 8. In general, the arrangement of centering means may be adapted to the offset required by any type of microtiter plate or test tube support plate comprising any number of wells or tubes. In particular, the offset between two plate reception zones may not be the same along the two directions of the array of light elements 44. Furthermore, the number of groups of centering means arranged on the support 42 may also be more than 2, so that a larger number of types of plates can be supported which may use different offsets.

Figure 9:
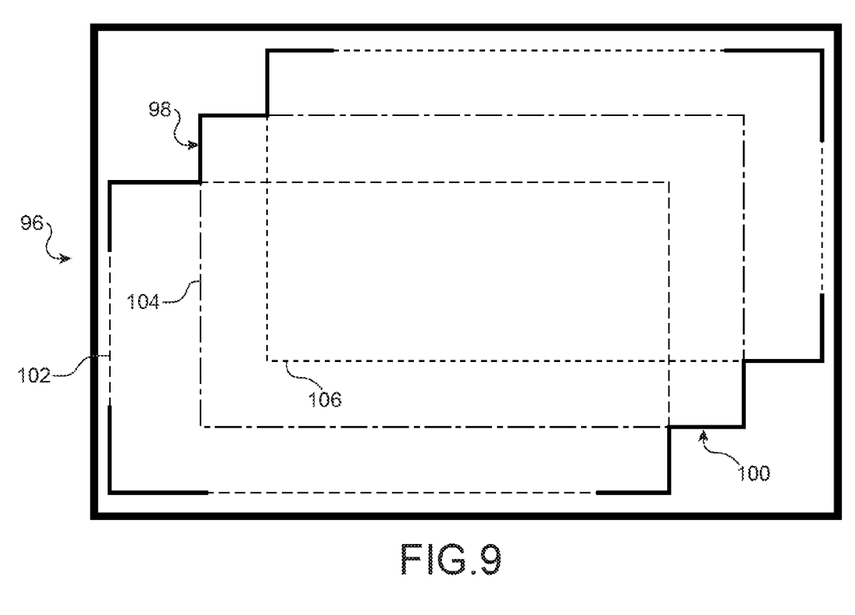
FIG. 9 shows a diagrammatic top view of a pipetting aid device in accordance with a second example embodiment.

FIG. 9 thus diagrammatically shows the arrangement of three groups of centering means on a pipetting aid device 96 similar to the device 40 described above. These centering means comprise two centering structures 98 and 100 common to the three groups of centering means. Each of the two centering structures 98 and 100 has a stepped surface forming six stop walls, each comprising three pairs of walls perpendicular to each other so as to define three zones 102, 104 and 106 to support at least three different types of plates.

The pipetting aid device may advantageously be associated with several different types of microtiter plates or test tube support plates, and may comprise the same number of groups of centering means to form a pipetting kit. Such a kit may include one or several pipettes and a plurality of plates. Furthermore, the pipetting aid device may comprise several assemblies of the type described above adjacent to each other and comprising a single common support so that several modules can be supported side by side at the same time.

Figure 10:
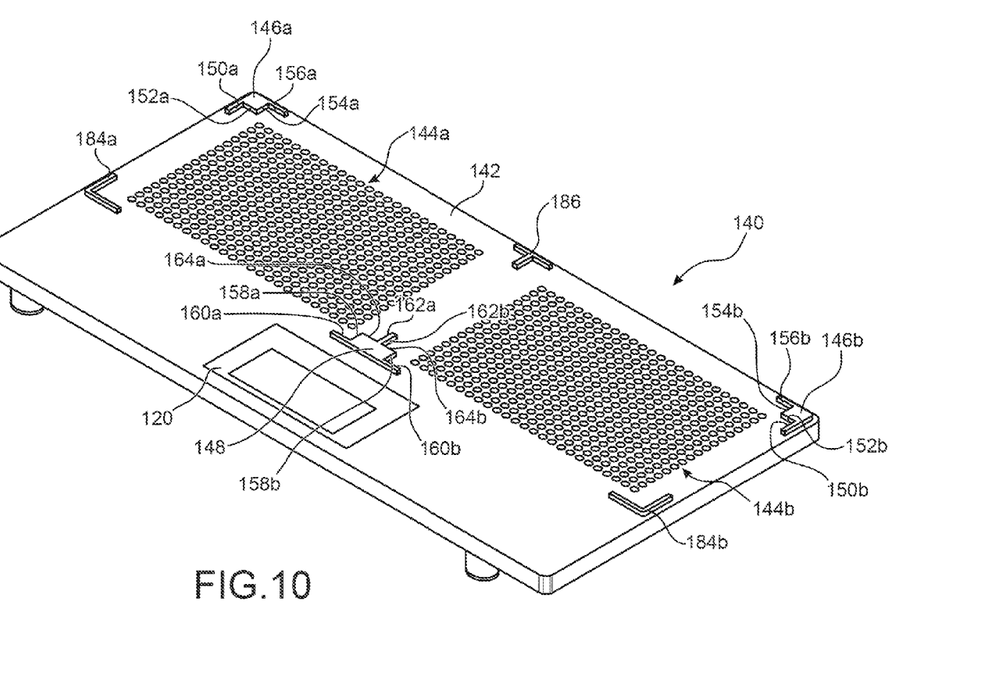
FIG. 10 shows a perspective view of a pipetting aid device in accordance with a third example embodiment.

For example, FIG. 10 shows a pipetting aid device 140 comprising two assemblies side by side to support two microtiter plates. With reference to FIG. 10, reference numbers marked with index "a" relate to elements belonging to one of the assemblies of the device, while references marked with index "b" relate to elements belonging to the other assembly. The device 140 comprises two matrices of light elements 144a and 144b side by side on the same support 142 common to the two assemblies of the device, and module centering elements similar to those described in the above arranged on the support 142 and associated with each of the two matrices of light elements 144a and 144b.

The module centering structures comprise two centering structures 146a and 146b similar to the centering element 46 in FIG. 3 arranged around the periphery of the device, and a centering structure 148 arranged between the two matrices of light elements 144a and 144b respectively. The centering structure 146a comprises stop walls 150a, 152a, 154a and 156a, and the centering structure 146b comprises stop walls 150b, 152b, 154b and 156b, so that modules can be centered facing the matrices of light elements 144a and 144b, respectively.

The centering structure 148 comprises first stop walls 158a, 160a, 162a and 164a designed to cooperate with the stop walls 150a, 152a, 154a and 156a of the centering element 146a, and also stop walls 158b, 160b, 162b and 164b configured to cooperate with the stop walls 150b, 152b, 154b and 156b of the centering structure 146b. The centering structure 148 is thus common to the two assemblies of the device.

As shown diagrammatically in FIG. 10, the device 140 also comprises additional module centering structures 184a, 184b and 186, that are similar to the structures 84 and 86 of the device 40. The device 140 also comprises control means 120 of the matrices of light elements 144a and 144b.

A device of the type described in FIG. 10 may for example be used advantageously to jointly monitor sampling operations for one or several liquids out of the wells of a first microtiter plate and to dispense these liquids into the wells of a second microtiter plate. In particular with this device, two microtiter plates comprising different numbers of wells can be used together, for example when it is required to take samples of several different reagents from a larger number of wells in the first plate and to combine them in the smaller number of wells in the second plate. The device guarantees the correct position of each plate relative to the corresponding array of light elements to give optimum operation monitoring quality.

A pipetting aid device has been described that includes at least one assembly that comprises a support that will receive approximately rectangular shaped modules that comprise orifices that will contain a liquid. The support comprises a plurality of light elements distributed in a two-dimensional matrix, and a number N (at least 2) of groups of module centering means arranged on the support for centering N distinct types of modules, respectively, in positions such that said modules respectively cover N support zones offset from each other. In an example embodiment, the centering means is arranged outside all of the support zones. The term "module" in this description refers to a microtiter plate or a test tube support plate, or a similar type of structure. In the first case, the orifices in the module are well entry orifices in the plate, while in the second case the module orifices are test tube assembly orifices. The relative offsets of the N zones can be defined to allow compensation of differences in the arrangement of orifices in different types of modules to enable a correct positioning of the orifices relative to light elements on the support.

Due to the plurality of groups of module centering means arranged on the device support, different types of modules can be positioned directly on the support, while assuring a good relative position of the orifices of the modules relative to the light elements on the support, based on an appropriate offset between the corresponding assembly positions of the different types of modules. Using the centering means, the pipetting aid device avoids the use of adaptors and the disadvantages mentioned above related to the use of adaptors.

In an example embodiment, compensation of position differences of the orifices in the different types of modules results in a small amplitude offset between the different zones such that the zones comprise a common part. In an example embodiment, each of said zones entirely covers all the light elements on the support so that the benefit of these light elements can be used regardless of the type of module used. The support zones may have approximately the same dimensions.

Since the dimensions of the zones are defined by the arrangement of module centering means, standard sized modules can be used. However, as a variant, the module centering means can be arranged to enable centering of modules with different dimensions.

In an example embodiment, the centering means include at least two centering structures that are arranged at the ends of a diagonal of the corresponding support zone and that have two stop walls orthogonal to each other. Centering means of this type can provide good support for the modules while remaining simple and inexpensive to manufacture.

In an example embodiment, the centering structures are formed from a single part with a right-angle corner surface. This type of centering structure has good mechanical strength and is compact, which is particularly advantageous in the case of small amplitude offsets between the module support zones.

In an example embodiment, each of the centering structures is common to all groups of centering means and has a stepped surface. In this way, the device may comprise a small number of centering structures with good mechanical strength and easy construction.

In general, module centering means are advantageously arranged so that center lines of orifices of the modules can be made to coincide with the respective light emission axes of at least some of the light elements of the support. As a variant, particularly in the case of a module of the type comprising orifices with a relatively large cross-section, the module centering means may also be arranged such that light elements are uniformly distributed about the axis of each of the orifices of the module.

In an example embodiment, a first group of centering means is configured to center a module comprising L×C liquid reception orifices on a first zone of the support, and a second group of centering means is configured to center a module comprising L/2×C/2 liquid reception orifices on a second zone of the support, there are L×C light elements on the support, and the second support zone is offset from the first zone by a distance equal to approximately 0.5 times the interval separating two consecutive light elements of the support, along each of the two directions of the matrix. In this case, the amplitude of the offset of the second support zone from the first zone is equal to the amplitude of the offset of the matrix of orifices in the second module relative to the matrix of orifices in the first module. Since the corresponding matrices of the orifices in the first module and the light elements of the support are similar, the two groups of centering means thus enable alignment of orifices in the first module and also orifices in the second module, with the light elements of the support.

In another example embodiment, there are (L+1)×(C+1) light elements on the support, and the second support zone is offset from the first zone by a distance equal to approximately 1.5 times the interval separating the two consecutive light elements of the support along the two directions of the matrix. Since in this case the amplitude of the offset between the matrix of orifices of the second module and the matrix of orifices of the first module is also equal to 0.5 times the interval separating two consecutive light elements on the support, in this case the amplitude of the offset of the second zone of the support from the first zone is equal to the sum of the offset amplitude of the matrix of orifices in the second module from the matrix of orifices in the first module, and the interval separating two consecutive light elements of the support. Due to a larger offset between the second support zone and the first one, this configuration makes it possible to increase the extent of the module centering means to improve how modules are supported by the centering means, without the module centering means hindering the module support zones.

If necessary depending on the arrangement of orifices in the second module, the support may comprise a row and a column of additional light elements such that the matrix of light elements of the support can cover all orifices in the second module.

The word "example" is used herein to mean serving as an example, instance, or illustration. Any aspect or design described herein as "example" is not necessarily to be construed as preferred or advantageous over other aspects or designs. Further, for the purposes of this disclosure and unless otherwise specified, "a" or "an" means "one or more".

The foregoing description of example embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A device comprising:
   a support comprising a first face;
   a plurality of light elements mounted in the support to form a two-dimensional array in the plane of the first face;
   a first centering structure mounted to extend from the first face of the support and comprising at least a first pair and a second pair of stop walls, wherein a pair of stop walls forms a corner; and
   a second centering structure mounted to extend from the first face of the support and comprising at least a third pair and a fourth pair of stop walls;
   wherein the first pair of stop walls and the third pair of stop walls form corners of a first positioning zone of a first type of plate and the second pair of stop walls and the fourth pair of stop walls form corners of a second positioning zone of a second type of plate; and
   further wherein the first centering structure and the second centering structure are positioned outside both the first positioning zone and the second positioning zone.

2. The device of claim 1, further comprising a plate of the first type of plate or a plate of the second type of plate.

3. The device of claim 1, further comprising a third centering structure mounted to extend from the first face of the support and comprising at least a fifth pair of stop walls wherein the fifth pair of stop walls forms a third corner of the first positioning zone of the first type of plate.

4. The device of claim 3, further comprising a fourth centering structure mounted to extend from the first face of the support and comprising at least a sixth pair of stop walls wherein the sixth pair of stop walls forms a third corner of the second positioning zone of the second type of plate.

5. The device of claim 2, wherein the plate of the first type of plate comprises orifices that align with a first portion of the plurality of light elements when the first type of plate is positioned in the first positioning zone.

6. The device of claim 5, wherein the plate of the second type of plate comprises orifices that align with a second portion of the plurality of light elements when the second type of plate is positioned in the second positioning zone, wherein the first portion of the plurality of light elements is different from the second portion of the plurality of light elements.

7. The device of claim 6, wherein the number of the orifices of the first type of plate is different than the number of the orifices of the second type of plate.

8. The device of claim 1, wherein the first centering structure further comprises a fifth pair of stop walls and the second centering structure further comprises a sixth pair of stop walls wherein the fifth pair of stop walls and the sixth pair of stop walls form corners of a third positioning zone of a third type of plate.

9. The device of claim 1, wherein the first positioning zone and the second positioning zone include the plurality of light elements.

10. The device of claim 1, wherein the first centering structure is diagonal to the second centering structure.

11. The device of claim 1, wherein the corners form right angles.

12. The device of claim 1, wherein the first centering structure and the second centering structure are removably mounted to the support.

13. The device of claim 1, wherein the first centering structure and the second centering structure are retractable into the first face of the support.

14. The device of claim 1, wherein the first pair of stop walls has a different length than the second pair of stop walls.

15. The device of claim 1, wherein a first stop wall of the first pair of stop walls has a different length than a second stop wall of the first pair of stop walls.

16. The device of claim 1, wherein the first type of plate is selected from the group consisting of a microtiter plate and a test tube support plate.

17. The device of claim 1, further comprising:
 a second plurality of light elements mounted in the support to form a second two-dimensional array in the plane of the first face; and
 a third centering structure mounted to extend from the first face of the support and comprising at least a fifth pair of stop walls;
 wherein the second centering structure further comprises a sixth pair of stop walls;
 wherein the fifth pair of stop walls and the sixth pair of stop walls form corners of a third positioning zone of a third type of plate and the third positioning zone includes the second plurality of light elements.

18. The device of claim 17, wherein the first type of plate and the third type of plate are the same type of plate.

19. The device of claim 1, further comprising a plate of the first type of plate comprising orifices or a plate of the second type of plate comprising orifices, wherein the number of the plurality of light elements is greater than the number of the orifices of the first type of plate and the number of the orifices of the second type of plate.

20. The device of claim 1, further comprising:
 a processor; and
 a computer-readable medium operably coupled to the processor, the computer-readable medium having instructions stored thereon that when executed by the processor cause the system to control the switching on and off of the plurality of light elements.

\* \* \* \* \*